(12) United States Patent
Bono et al.

(10) Patent No.: US 10,582,933 B2
(45) Date of Patent: Mar. 10, 2020

(54) OSCILLATING SURGICAL CUTTING TOOL

(71) Applicant: Peter L. Bono, Bingham Farms, MI (US)

(72) Inventors: Peter L. Bono, Bingham Farms, MI (US); James D. Lark, West Bloomfield, MI (US); John S. Scales, Ann Arbor, MI (US)

(73) Assignee: Capstone Surgical Techologies, LLC, Bingham Farms, MI (US)

( * ) Notice: Subject to any disclaimer, the term of this patent is extended or adjusted under 35 U.S.C. 154(b) by 166 days.

(21) Appl. No.: 15/928,885

(22) Filed: Mar. 22, 2018

(65) Prior Publication Data

US 2019/0290290 A1 Sep. 26, 2019

(51) Int. Cl.
*A61B 17/14* (2006.01)
*A61B 17/16* (2006.01)
(Continued)

(52) U.S. Cl.
CPC .......... *A61B 17/144* (2016.11); *A61B 17/162* (2013.01); *A61B 17/1659* (2013.01); *A61B 17/32002* (2013.01); *A61B 17/1615* (2013.01); *A61B 17/1624* (2013.01); *A61B 17/1633* (2013.01); *A61B 17/1637* (2013.01); *A61B 2017/00261* (2013.01); *B27B 19/006* (2013.01)

(58) Field of Classification Search
CPC ..... A61B 17/320758–320775; A61B 17/1615; A61B 17/1617; A61B 17/1631; A61B 17/1633; A61B 17/1637; A61B 2017/320028; B27B 19/006; B24D 5/123; B23D 61/02–10; B23B 2251/406; B23B 2251/241
See application file for complete search history.

(56) References Cited

U.S. PATENT DOCUMENTS 1,154,159 A 9/1915 Ashworth
1,979,905 A * 11/1934 Rogerson ................. B24D 5/00
451/542

(Continued)

FOREIGN PATENT DOCUMENTS

AR 42807 7/2005
AT 370608 4/1983
(Continued)

OTHER PUBLICATIONS

MasterCut Tool Corp., Bur Series, Metric, (2018).
(Continued)

*Primary Examiner* — Tan-Uyen T Ho
*Assistant Examiner* — Charles M Wei
(74) *Attorney, Agent, or Firm* — McHale & Slavin, P.A.

(57) ABSTRACT

The present invention provides a cutting tool for surgical procedures. More specifically, the present invention provides a rotary surgical cutting tool which overcomes the disadvantages of prior art surgical cutting tools by providing a rotary cutting tool having straight flutes, with each side of the flute being provided with a cutting edge that permits cutting in both directions during limited oscillatory motion of the rotary surgical cutting tool. The areas between the cutting edges are provided with relief to reduce friction while the flute moves the cut material away from the cutting edges.

17 Claims, 13 Drawing Sheets

(51) Int. Cl.
*A61B 17/32* (2006.01)
*B27B 19/00* (2006.01)
*A61B 17/00* (2006.01)

(56) References Cited

U.S. PATENT DOCUMENTS

| | | | | |
|---|---|---|---|---|
| 2,029,114 | A * | 1/1936 | Milne | B23D 61/023 125/22 |
| 2,557,429 | A | 6/1951 | Hawley | |
| 2,659,398 | A * | 11/1953 | Marvin | B23D 61/025 83/837 |
| 2,795,247 | A * | 6/1957 | Topolinski | B23D 61/021 83/848 |
| 2,815,746 | A * | 12/1957 | Schwarzkopf | B28D 1/121 125/22 |
| 2,831,295 | A | 4/1958 | Weiss | |
| 3,064,399 | A * | 11/1962 | Anderson | B24D 5/123 451/542 |
| 3,128,755 | A * | 4/1964 | Benson | B28D 1/121 125/15 |
| 3,203,140 | A * | 8/1965 | Hallez | B24D 5/123 451/541 |
| 3,347,289 | A * | 10/1967 | Zizka | B23D 45/105 83/876 |
| 3,577,579 | A | 5/1971 | Duve et al. | |
| 3,657,845 | A * | 4/1972 | Sekiya | B24D 5/06 451/541 |
| 3,937,222 | A * | 2/1976 | Banko | A61F 9/00763 606/170 |
| 4,081,704 | A | 3/1978 | Vassos et al. | |
| 4,111,208 | A | 9/1978 | Leuenberger | |
| 4,267,814 | A * | 5/1981 | Benson | B23D 61/021 125/15 |
| 4,461,198 | A * | 7/1984 | Grassmann | B23D 61/02 83/835 |
| 4,550,708 | A * | 11/1985 | Roemmele | B23D 61/021 125/15 |
| 4,705,017 | A * | 11/1987 | Lewis | B23D 61/021 125/15 |
| 4,706,659 | A * | 11/1987 | Matthews | A61B 17/164 464/173 |
| 4,739,745 | A * | 4/1988 | Browning | B28D 1/121 125/15 |
| 4,854,295 | A * | 8/1989 | Sakarcan | B23D 61/021 125/15 |
| 4,932,935 | A | 6/1990 | Swartz | |
| 5,018,276 | A * | 5/1991 | Asada | B23D 65/00 30/347 |
| 5,184,597 | A * | 2/1993 | Chiuminatta | B24D 5/123 125/15 |
| 5,522,829 | A | 6/1996 | Michalos | |
| 6,015,420 | A * | 1/2000 | Wulfman | A61B 17/320758 604/22 |
| 6,021,538 | A | 2/2000 | Kressner et al. | |
| 6,321,738 | B1 * | 11/2001 | Walsh | B23D 61/025 125/15 |
| 6,422,229 | B1 * | 7/2002 | Padrinao | B23D 61/021 125/13.01 |
| 6,721,986 | B2 | 4/2004 | Zhuan | |
| 6,790,215 | B2 * | 9/2004 | Findlay, III | A61B 17/320758 606/159 |
| 6,878,051 | B2 * | 4/2005 | Brach | B23D 61/021 451/542 |
| 7,922,720 | B2 | 4/2011 | May et al. | |
| 8,007,506 | B2 * | 8/2011 | To | A61B 17/32075 606/159 |
| 8,943,634 | B2 | 2/2015 | Sokol et al. | |
| 2001/0005909 | A1 * | 6/2001 | Findlay, III | A61B 17/32075 800/3 |
| 2002/0194975 | A1 * | 12/2002 | Bishop | B23D 61/021 83/851 |
| 2004/0050603 | A1 | 3/2004 | Jaeger | |
| 2005/0283175 | A1 | 12/2005 | Tanner et al. | |
| 2006/0130622 | A1 * | 6/2006 | Holmes | B23D 61/028 83/13 |
| 2006/0229624 | A1 | 10/2006 | May et al. | |
| 2008/0108010 | A1 | 5/2008 | Wang | |
| 2009/0177202 | A1 | 7/2009 | May et al. | |
| 2011/0015635 | A1 | 1/2011 | Aryan | |
| 2011/0196404 | A1 | 8/2011 | Dietz et al. | |
| 2011/0295270 | A1 | 12/2011 | Giordano et al. | |
| 2012/0211546 | A1 | 8/2012 | Shelton, IV | |
| 2013/0245629 | A1 | 9/2013 | Xie | |
| 2015/0119916 | A1 | 4/2015 | Dietz et al. | |
| 2015/0135915 | A1 * | 5/2015 | Mann | B24D 5/123 83/13 |
| 2017/0231643 | A1 * | 8/2017 | Victor | A61B 17/164 606/80 |
| 2018/0042618 | A1 * | 2/2018 | Victor | A61B 17/1615 |

FOREIGN PATENT DOCUMENTS

| | | |
|---|---|---|
| AU | 2003200831 | 1/2003 |
| AU | 2011215901 | 2/2011 |
| BE | 861446 | 3/1978 |
| CA | 1112970 | 11/1981 |
| CA | 2513071 | 7/2004 |
| CA | 2788918 | 8/2011 |
| CH | 610753 | 5/1979 |
| CL | 252004 | 3/2005 |
| CN | 1338910 | 3/2002 |
| CN | 2629654 | 8/2004 |
| CN | 10126774 | 9/2008 |
| CN | 101267774 | 9/2008 |
| CN | 102781349 | 11/2012 |
| DE | 570977 | 2/1933 |
| DE | 2730227 | 6/1978 |
| EP | 148304 | 9/1987 |
| EP | 261260 | 3/1988 |
| EP | 1581374 | 8/2006 |
| EP | 1937160 | 7/2008 |
| EP | 1690649 | 1/2009 |
| EP | 2533703 | 12/2012 |
| ES | 465719 | 12/1980 |
| FI | 773650 | 6/1978 |
| FR | 2374886 | 7/1978 |
| GB | 1550577 | 8/1979 |
| GB | 2430396 | 3/2007 |
| IT | 1081824 | 5/1985 |
| JP | S5380789 | 7/1978 |
| JP | S5613462 | 7/1978 |
| JP | 2006512954 | 4/2006 |
| JP | 4481173 | 6/2010 |
| JP | 2013519434 | 5/2013 |
| JP | 5826771 | 12/2015 |
| KR | 20070119513 | 12/2007 |
| KR | 20080070631 | 7/2008 |
| KR | 1333472 | 11/2013 |
| NL | 7713563 | 6/1978 |
| NO | 774411 | 6/1978 |
| WO | WO9107116 | 5/1991 |
| WO | WO2002015799 | 2/2002 |
| WO | WO2004062863 | 7/2004 |
| WO | WO2007008703 | 1/2007 |
| WO | WO2007039141 | 4/2007 |
| WO | WO2009151926 | 12/2009 |
| WO | WO2011100313 | 8/2011 |
| WO | WO2012166476 | 12/2012 |
| WO | WO2014150514 | 9/2014 |
| WO | WO2015006296 | 1/2015 |

OTHER PUBLICATIONS

MasterCut Tool Corp., Bur Series, US, (2010).
News & Notes, British Dental Journal, vol. 191, No. 7, pp. 410-411 (Oct. 13, 2001).
Tungsten Carbide Drills Mills & Burs, Internet catalogue, http://chinatungsten.com/picture-bank/tungsten-carbide-drills.html, (Retrieved Feb. 7, 2018).

(56) References Cited

OTHER PUBLICATIONS

Cutting Tool, Drill Bit, End Mill, Internet catalogue, http://lzqtool.com/include/search.aspx?keycode=c-grade&type=1&language=en, (Retrieved Feb. 7, 2018).

* cited by examiner

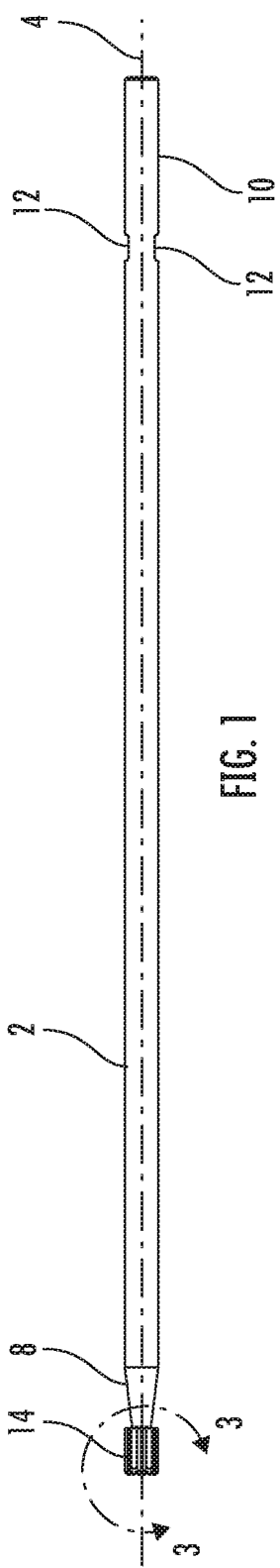
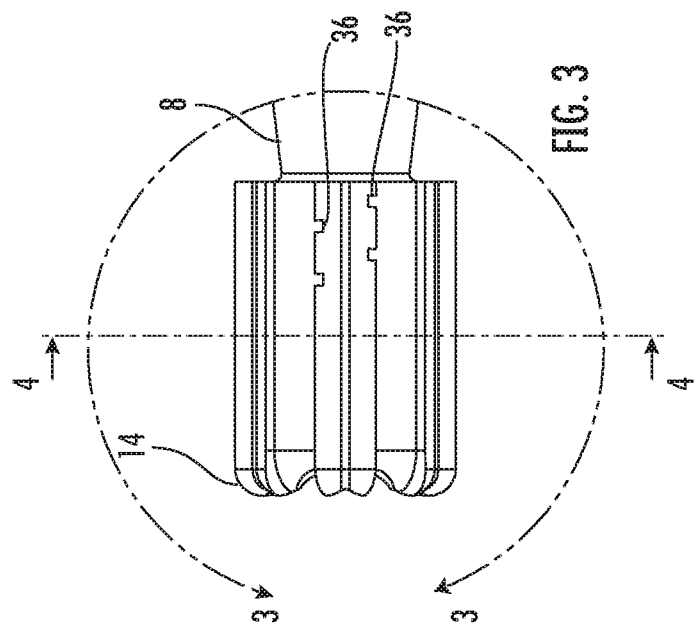
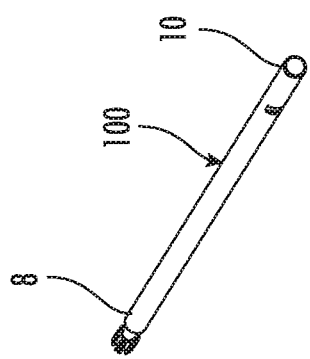

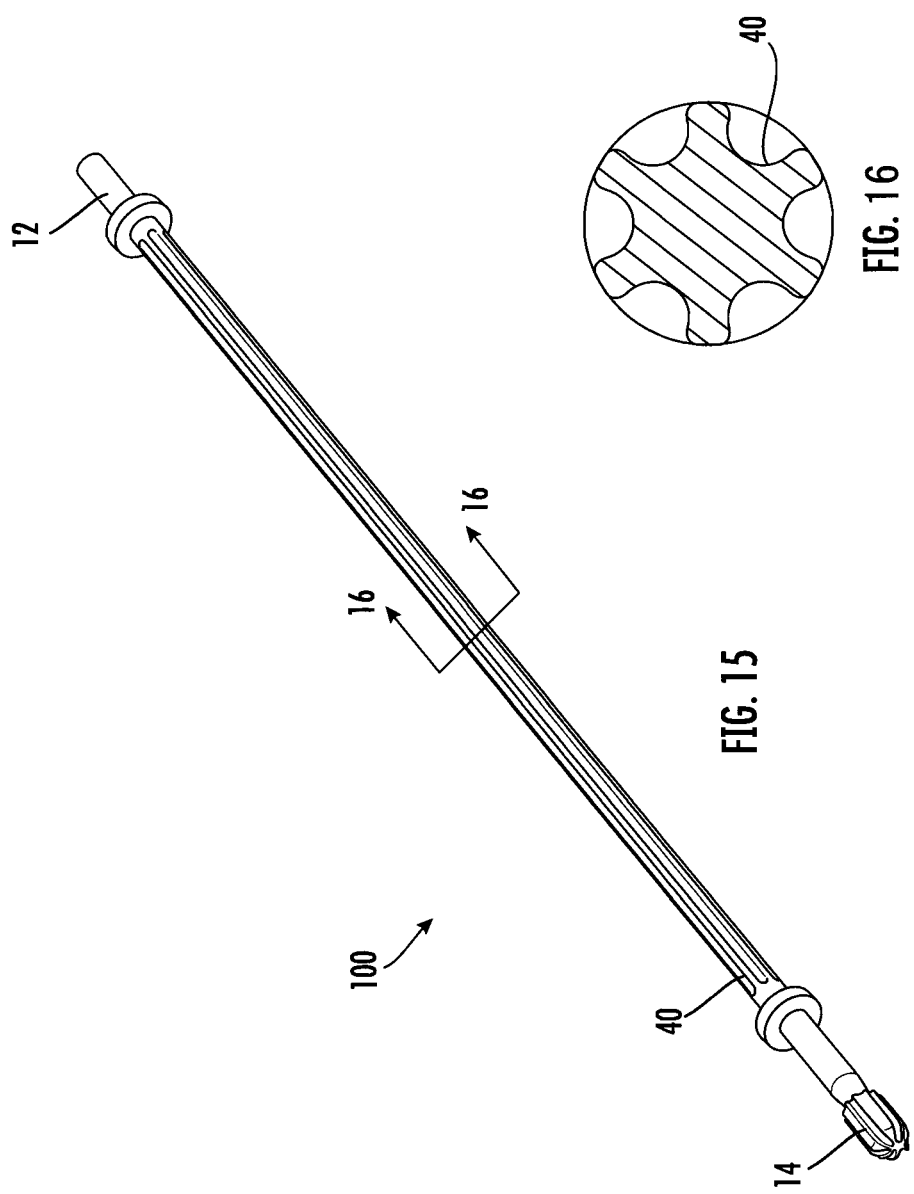

OSCILLATING SURGICAL CUTTING TOOL

FIELD OF INVENTION

The present invention generally relates to cutting tools; and more particularly, to a cutting tool having straight flutes and being constructed to cut when oscillated in a rotary motion in either direction around a longitudinal axis.

BACKGROUND INFORMATION

The prior art has provided cutting tools that remove material when rotated. These tools typically include one or more helix cut into the tool; the helix all arranged in the same direction and parallel if more than one helix is present. The helix may be cut for left hand rotation or for right hand rotation of the tool. The leading edge of each helix is provided with a sharpened edge that cuts the material when rotated, while the helix moves the cut material away from the cutting action. The rear edge of the helix is provided with relief so as not to drag on the edge of the cut surface.

U.S. Pat. No. 9,232,953 issued to Bono, the inventor of the present cutting tool, provides a cutting tool for bone, cartilage and disc material that includes at least one helix arranged in a first direction and at least one helix arranged in a second direction so that the cutting tool can be oscillated back and forth to cut. However, it has been found that this construction may not remove material fast enough during oscillation for some surgical procedures.

Therefore, it would be desirable to provide a rotary cutter configuration that cuts both directions when oscillated back and forth to quickly cut bone, cartilage and disc, while minimizing any form of change to soft tissues during removal of the bone, cartilage and disc tissue.

Thus, the present invention provides a surgical rotary cutting tool which overcomes the disadvantages of prior art surgical cutting tools by providing a rotary surgical cutting tool having straight flutes with each side of the flute being provided with a cutting edge to provide cutting in both directions during limited oscillatory motion.

SUMMARY OF THE INVENTION

Briefly, the present invention provides a cutting tool for surgical procedures. More specifically, the present invention provides a rotary surgical cutting tool which overcomes the disadvantages of prior art surgical cutting tools by providing a rotary cutting tool having straight flutes with each side of the flute being provided with a cutting edge that permits cutting in both directions during limited oscillatory motion of the rotary surgical cutting tool. The areas between the cutting edges are provided with relief to reduce friction while the flute moves the cut material away from the cutting edges.

Accordingly, it is an objective of the present invention to provide a rotary surgical cutting tool that functions to cut bone, cartilage and disc materials.

It is a further objective of the present invention to provide a rotary surgical cutting tool that cuts bone, cartilage and disc materials when oscillated back and forth about a central axis, cutting when moved in both directions.

It is yet a further objective of the present invention to provide a rotary surgical cutting tool that cuts bone, cartilage and disc materials, and cutting in both directions when oscillated through limited oscillatory motion.

It is another objective of the present invention to provide a rotary surgical cutting tool having straight flutes, wherein each flute is provided with two opposing cutting surfaces.

Other objectives and advantages of this invention will become apparent from the following description taken in conjunction with the accompanying drawings wherein are set forth, by way of illustration and example, certain embodiments of this invention. The drawings constitute a part of this specification, include exemplary embodiments of the present invention, and illustrate various objects and features thereof.

BRIEF DESCRIPTION OF THE FIGURES

FIG. 1 is a side view of one embodiment of the present device;

FIG. 2 is a top rear perspective view of the embodiment shown in FIG. 1;

FIG. 3 is a partial side view of the embodiment shown in FIG. 1, taken along lines 3-3, illustrating the cutter portion of the surgical cutting tool;

FIG. 15 is a perspective view of an alternative embodiment of the surgical cutting tool;

FIG. 16 is a section view, taken along lines 16-16 of FIG. 15, illustrating the cross sectional shape of the fluted shank;

DETAILED DESCRIPTION OF THE PREFERRED EMBODIMENTS

Figure 4:
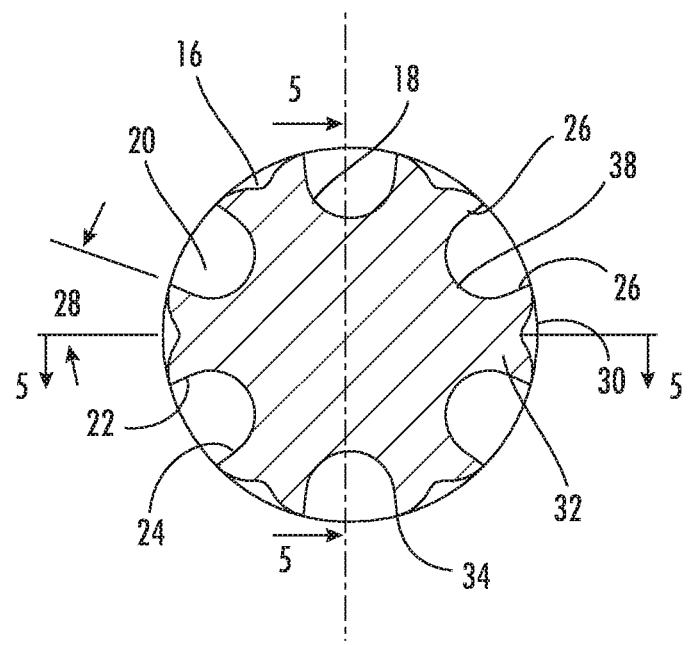
FIG. 4 is a partial front view, taken along lines 4-4 of FIG. 3, illustrating the construction of the cutting surfaces.
Figure 5:
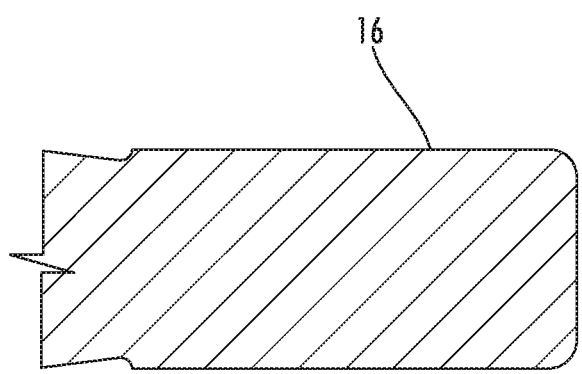
FIG. 5 is a partial section view taken along lines 5-5 of FIG. 4.
Figure 6:
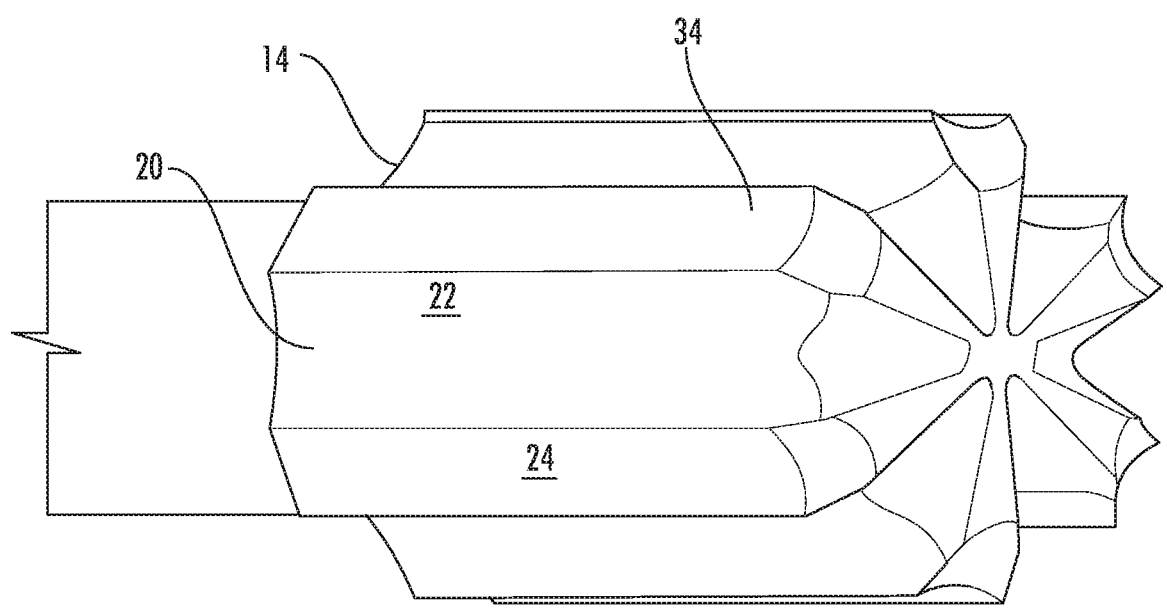
FIG. 6 is a partial perspective view of an alternative embodiment of the surgical cutting tool.
Figure 7:
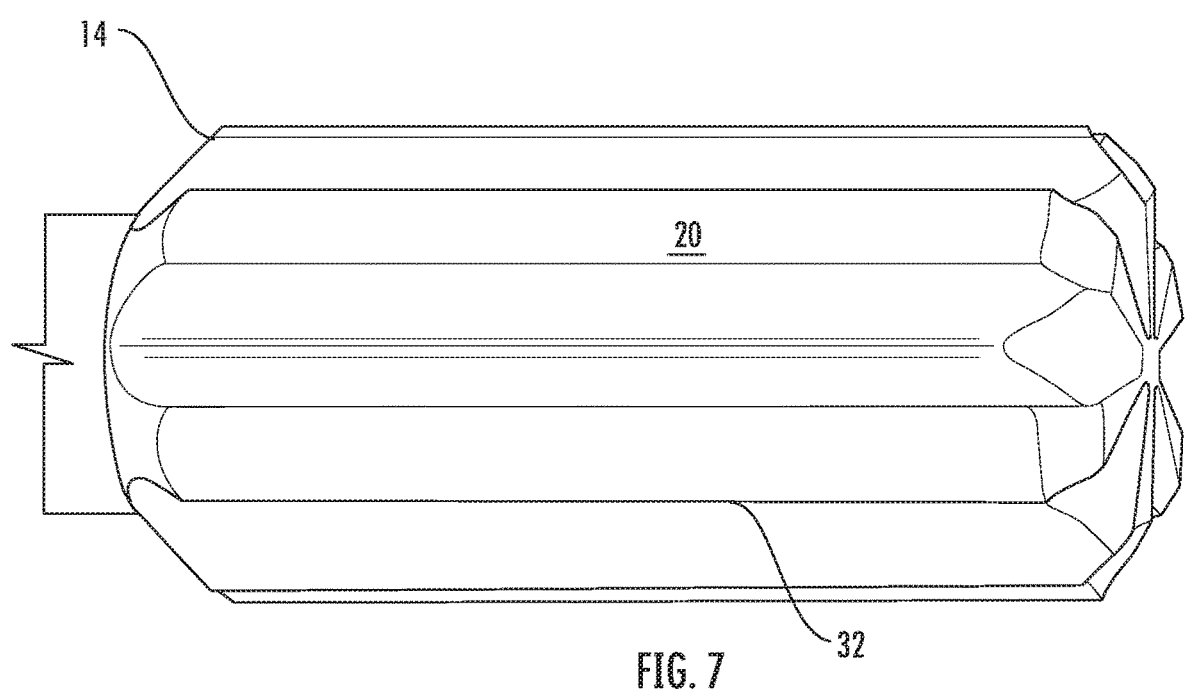
FIG. 7 is another perspective view of the embodiment illustrated in FIG. 6.
Figure 8:
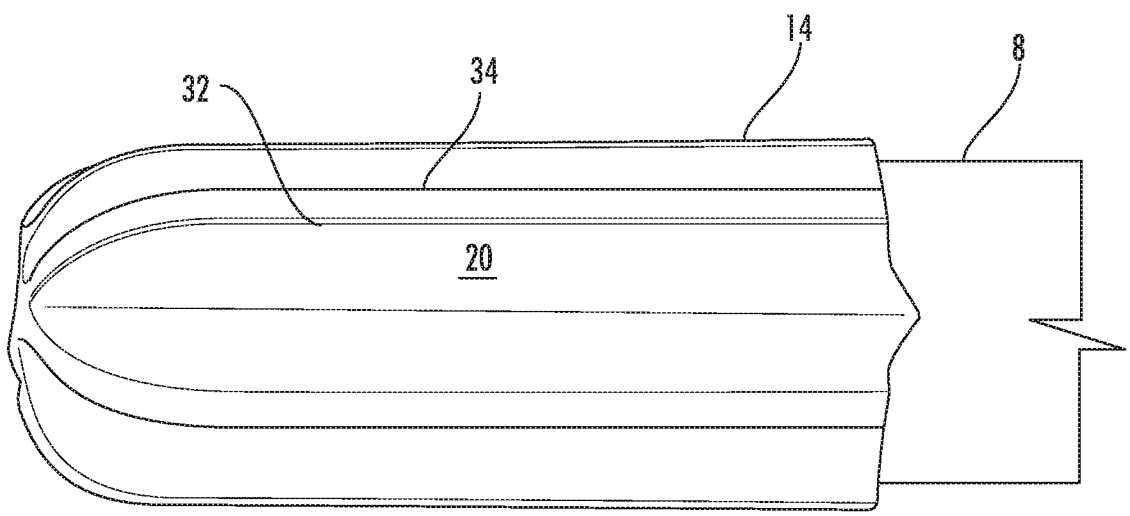
FIG. 8 is an alternative embodiment of the surgical cutting tool.
Figure 9:
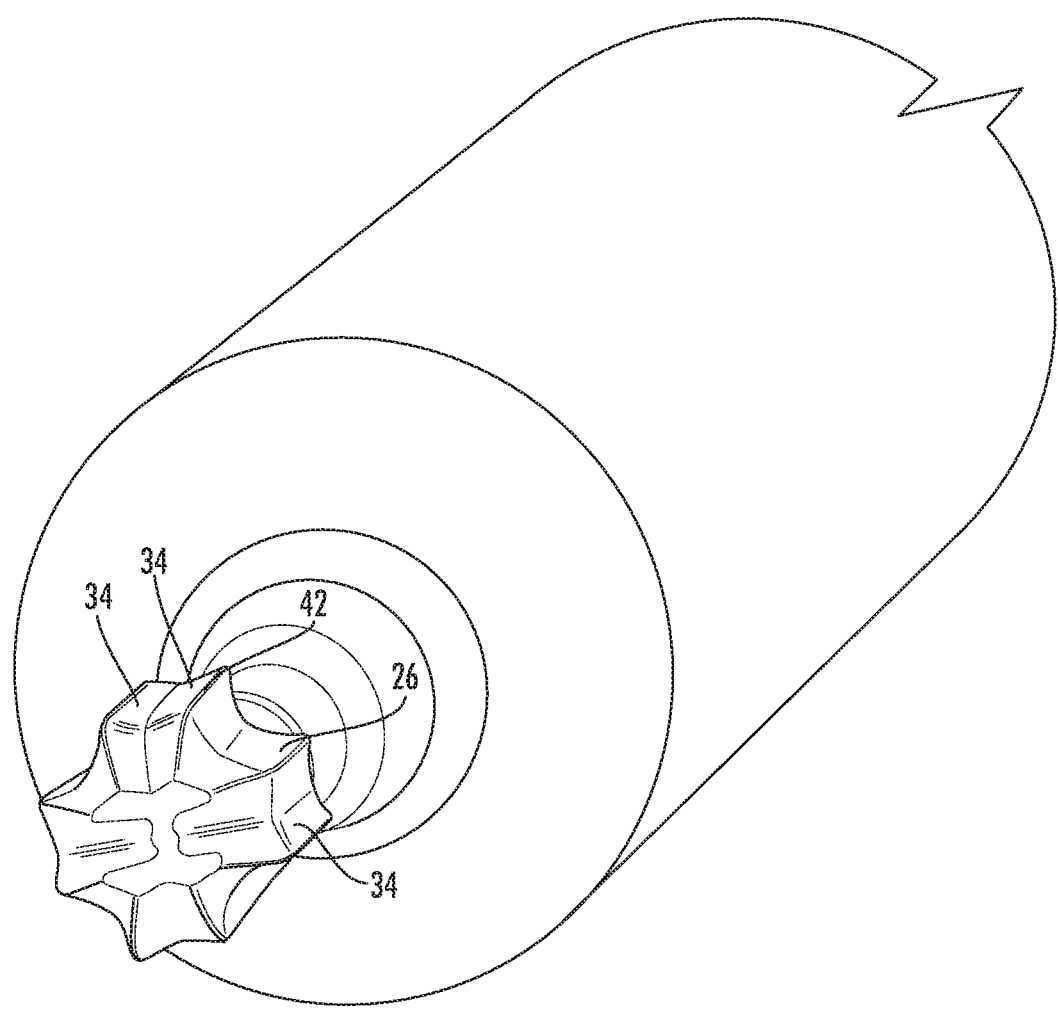
FIG. 9 is a perspective end view of the embodiment illustrated in FIG. 8.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiments illustrated.

Figure 10:
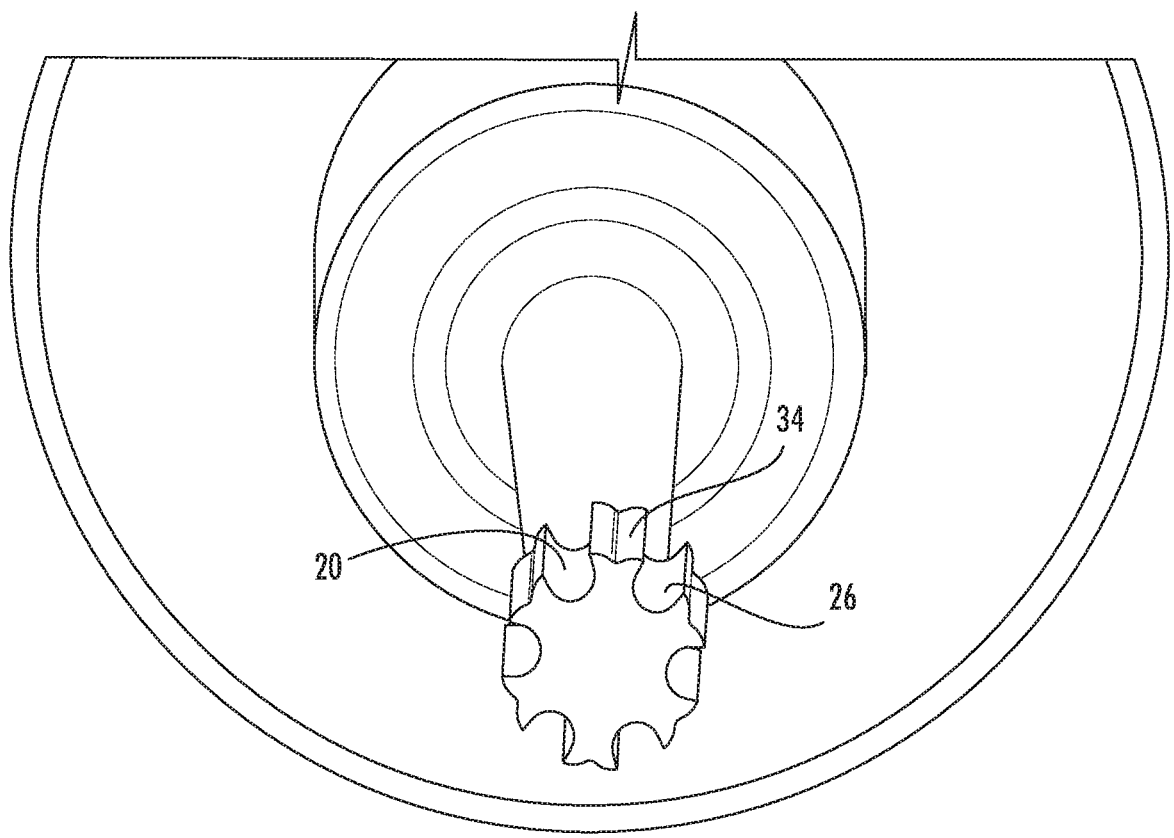
FIG. 10 is a perspective end view of an alternative embodiment of the surgical cutting tool.
Figure 11:
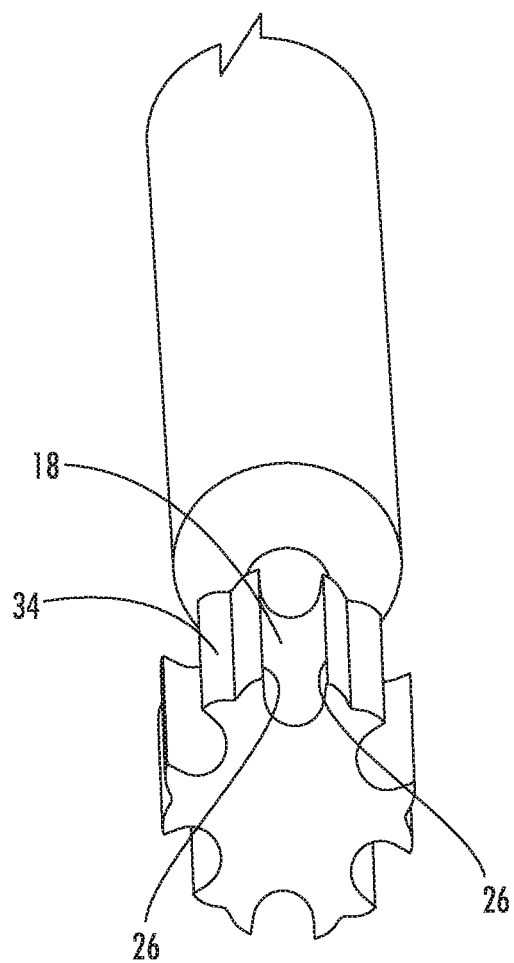
FIG. 11 is an end, side perspective view of the embodiment illustrated in FIG. 10.
Figure 12:
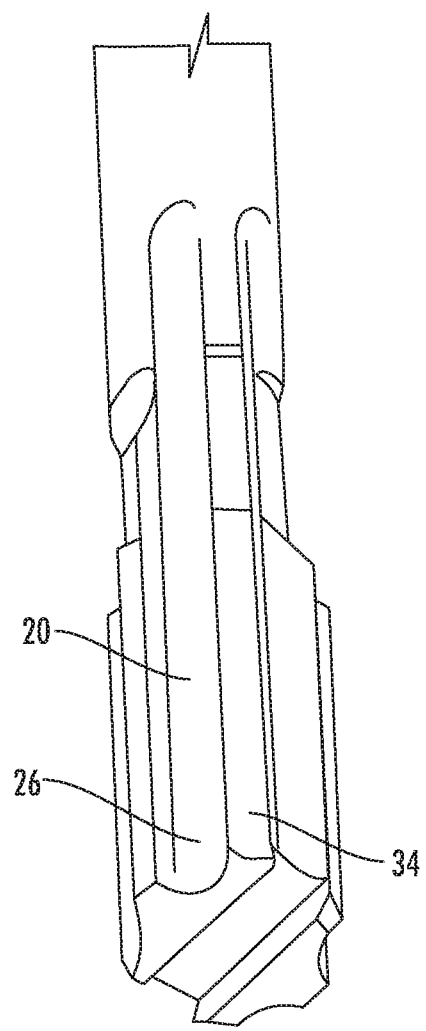
FIG. 12 is an end, side perspective view of an alternative embodiment of the surgical cutting tool.
Figure 13:
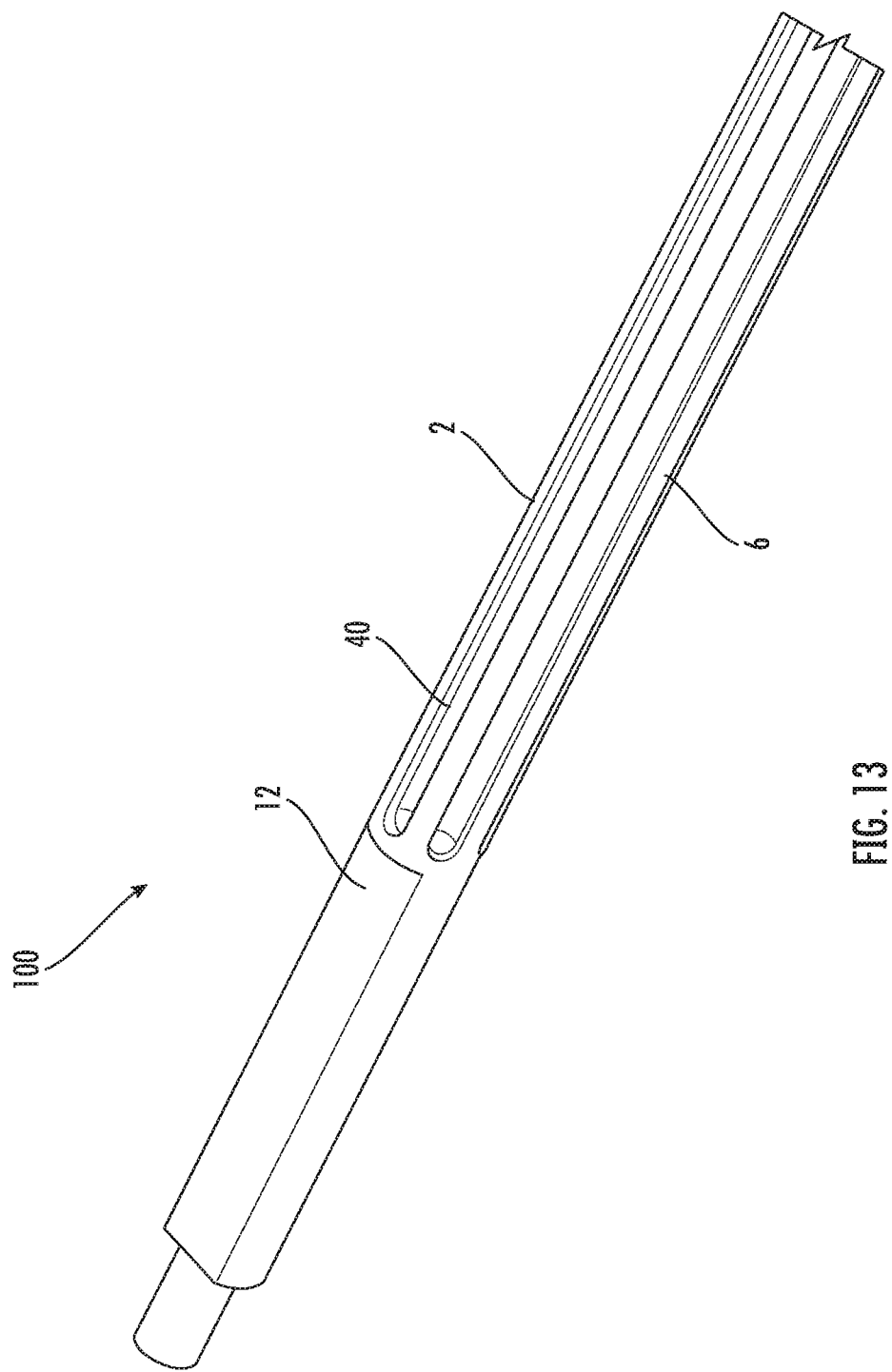
FIG. 13 is a partial perspective view of an alternative embodiment of the present invention, illustrating a fluted shank.
Figure 14:
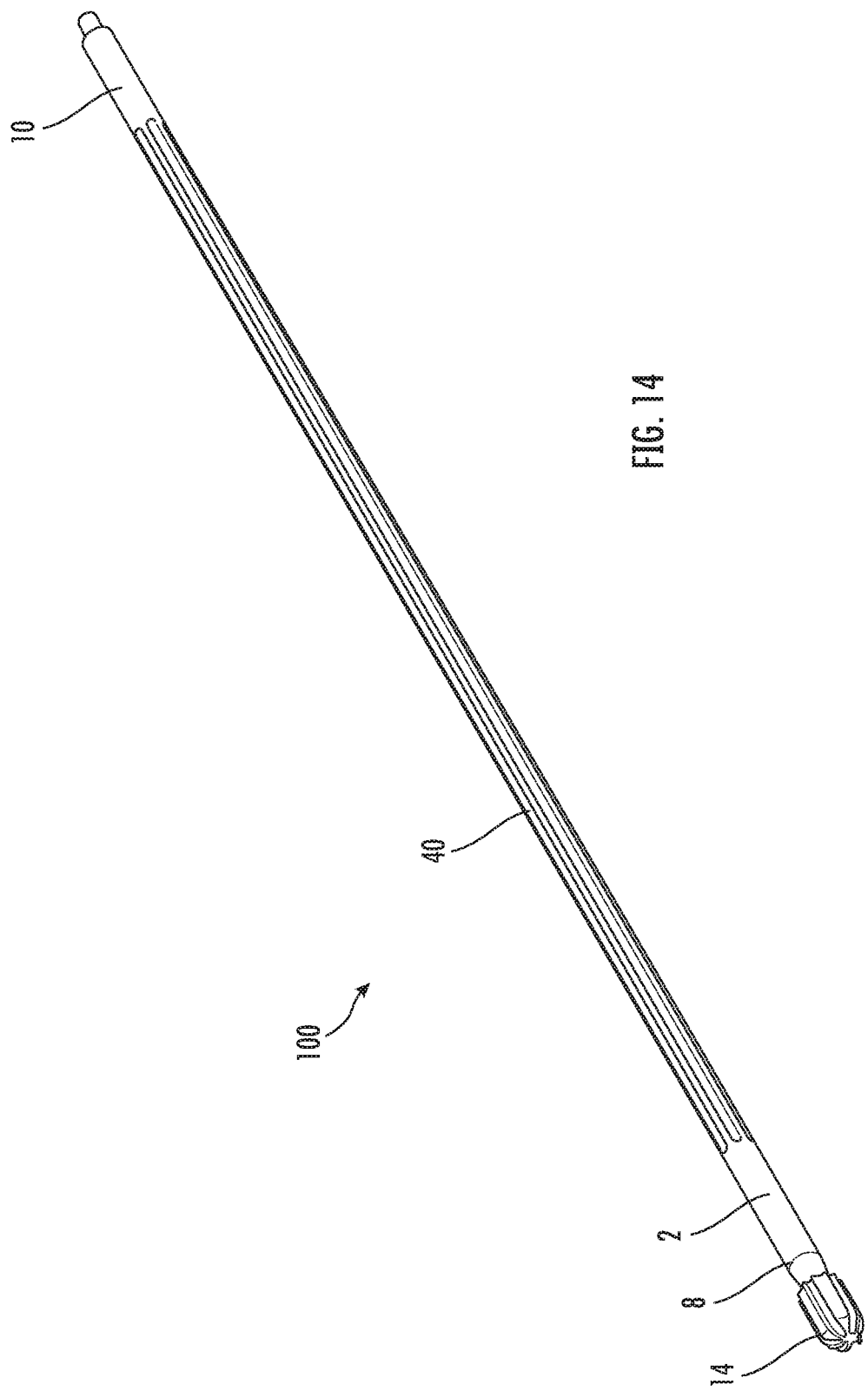
FIG. 14 is a perspective view of the embodiment illustrated in FIG. 13.
Figure 17:
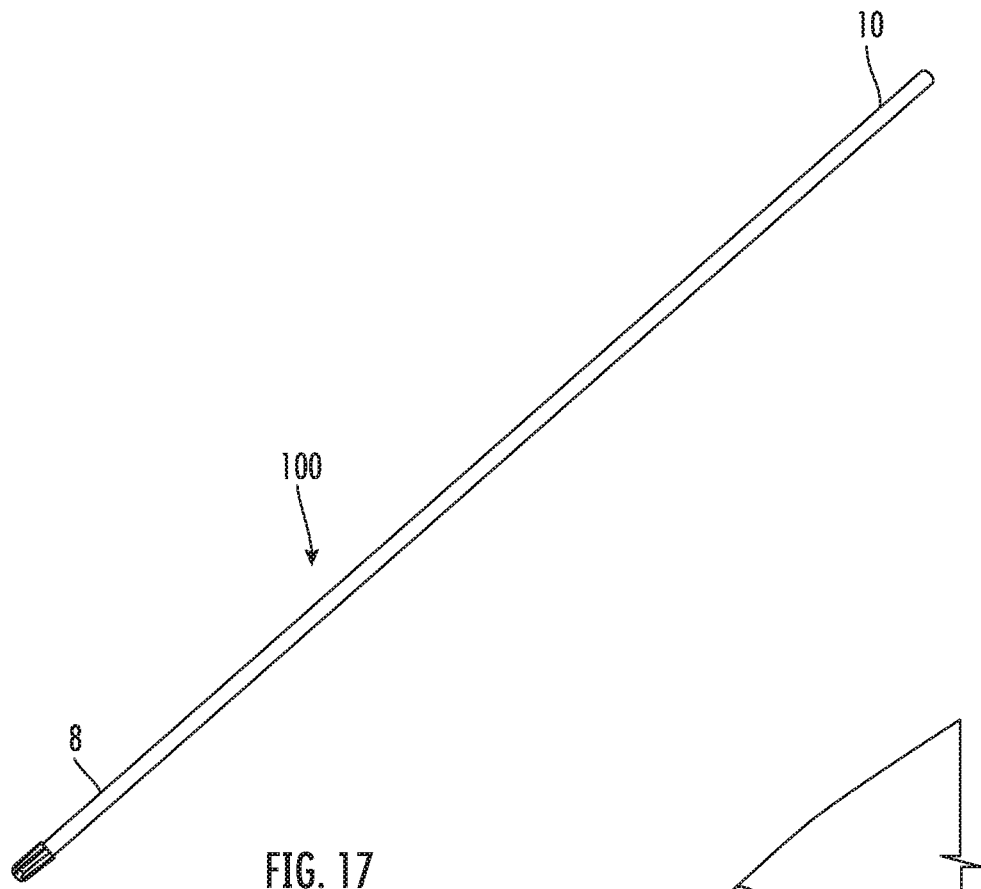
FIG. 17 is a perspective view of the embodiment illustrated in FIG. 15, illustrated without the bearings.

Referring generally to FIGS. 1-18, a surgical cutting tool 100 for cutting bone and tissue is illustrated. The surgical cutting tool includes a shank 2 having a longitudinal axis 4, a first end 8, and a second end 10. The shank 2 has a perimeter surface 6 (FIG. 13) extending around the longitudinal axis 4 and being symmetrically shaped to allow at least the second end 10 of the perimeter surface 6 to be gripped for rotation about the longitudinal axis 4. Thus, the longitudinal axis 4 is also a rotational axis. In a preferred embodiment, the second end of the shank 10 is round to cooperate with collets, sleeves, drill chucks and the like, as is known in the art. In at least one embodiment, the second end of the shank 10 includes one or more flats 12. The flats 12 are constructed and arranged to cooperate with set screws, tangent pins or the like (not shown) to assure that the surgical cutting tool 100 oscillates the same speed and arc of rotation as the reciprocating grinder 50 (FIG. 18) driving the surgical cutting tool 100. The first end 8 of the shank 2 includes a cutter 14, the cutter including an outside diameter 16; the cutter 14 including two or more flutes 18, each flute 18 extending parallel to the longitudinal axis 4 and extending inward from the outside diameter 16 toward the longitudinal axis 4, forming a recessed flute channel 20; each flute channel 20 having a pair of opposing sidewalls 22, 24 and a cylindrical radius at the base of each flute. Each sidewall forms a face 26 of a cutting edge 42 extending along the length of each flute channel 20 so that each flute channel 20 provides two opposing faces 26 providing cutting edges 42, allowing the cutter to cut in both directions when rotationally oscillated around the longitudinal axis 4. To enhance the cutting action and reduce pressure on the cutter 14, each face 26 includes a rake angle 28, said rake angle being divergent with respect to a center plane 30 extending through said longitudinal/rotational axis 4 when the blade 32 is centered with respect to the center plane 30, and wherein the rake angle 28 is convergent with respect to said center plane 30 when said flute 18 is centered with respect to said center plane 30. Each said blade 32 includes a top rake 34, said top rake 34 extending inwardly from said outside diameter 16 towards said axis of rotation 4 so that the convergence of the face 26 and the top rake 34 provides the outermost diameter of said cutter 14. In at least some embodiments, the top rake 34 is formed by a radius positioned to provide relief behind the face 26 as the cutter 14 is oscillated. In at least some embodiments, the face 26 and top rake 34 may include notches 36 or waves suitable to break the face 26 into shorter segments, thereby reducing load on the face 26 of the cutter 14. These notches 36 may be aligned or, more preferably, offset with respect to each other to eliminate ribs on the cut surface. The cutter 14 may be formed with an even or an odd number of flutes without departing from the scope of the invention. In general, a cutter 14 with a higher number of flutes will remove material faster than a cutter with fewer flutes. The cutter 14 may be formed of the same material and formed integral with the shank 2. Alternatively, the shank 2 and the cutter 14 may be constructed from different materials, and the cutter 14 may be cemented to the shank 2 with silver solder or the like suitable to secure the cutter 14 to the shank 2. In this manner, materials such as high speed steel and/or carbide may be utilized as desired without departing from the scope of the invention. Coatings known in the art such as, but not limited to, titanium nitride, titanium carbonitride, vanadium carbide and the like, having a higher hardness than the base material may be utilized. The flutes 18 may extend around the end of the cutter as illustrated in FIGS. 1-9, or alternatively, the end of the cutter may not be constructed to cut as illustrated in FIGS. 10-12.

Referring to FIGS. 13-17, an alternative embodiment of the present device is illustrated. In this embodiment, the shank 2 is constructed to include shank flutes 40. The shank flutes 40 extend along the length of the shank 2 and extend inwardly from the outer diameter 16 to reduce the rotating weight of the surgical cutting tool 100. In this manner, the surgical cutting tool 100 can be oscillated at faster speeds, reducing the inertia of the surgical cutting tool as its direction is changed. The shank flutes 40 may be constructed as flats, channels or any other shape suitable for reducing the rotating mass of the shank without departing from the scope of the invention.

Figure 18:
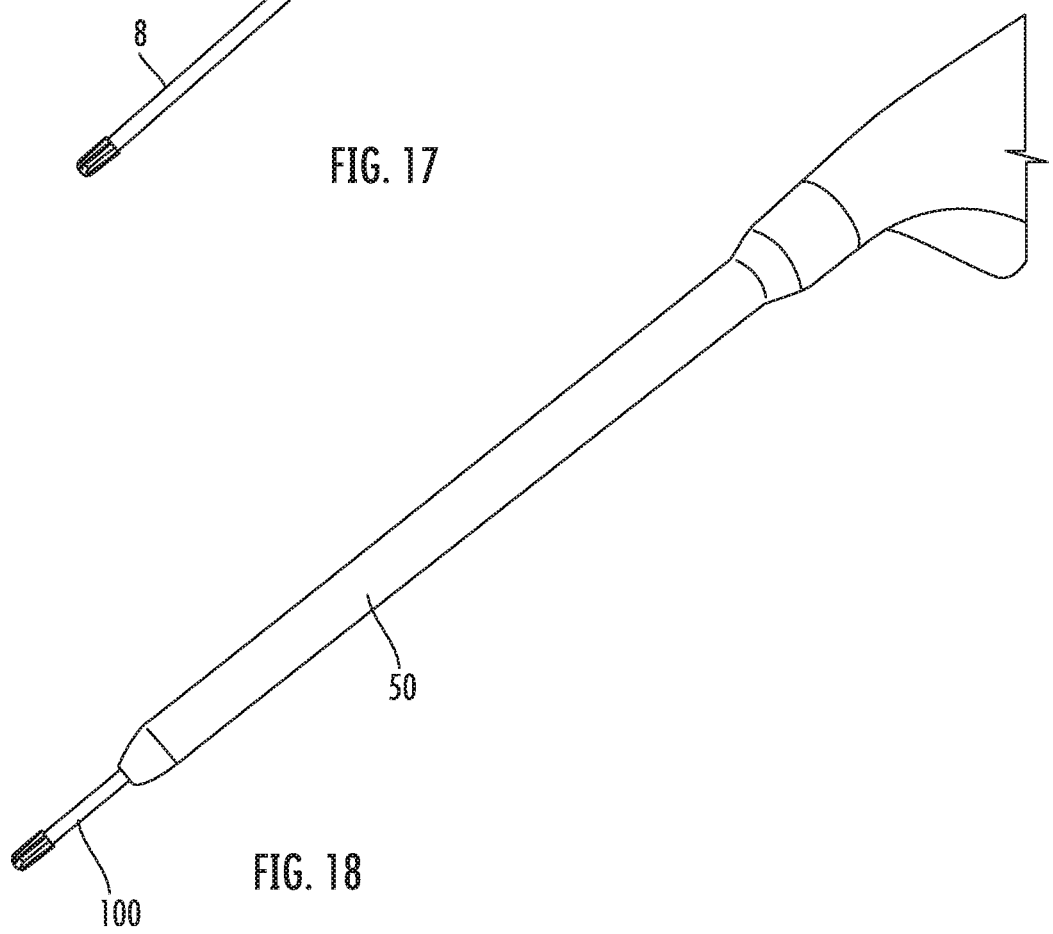
FIG. 18 is a partial perspective view illustrating the surgical cutting tool positioned within a reciprocating grinder.

Referring to FIG. 18, the surgical cutting tool 100 is illustrated within an oscillating grinder. Such a grinder is described in U.S. Pat. No. 9,232,953, granted to the owners of the present application.

It is to be understood that while a certain form of the invention is illustrated, it is not to be limited to the specific form or arrangement of parts herein described and shown. It will be apparent to those skilled in the art that various changes may be made without departing from the scope of the invention, and the invention is not to be considered limited to what is shown and described in the specification.

One skilled in the art will readily appreciate that the present invention is well adapted to carry out the objects and obtain the ends and advantages mentioned, as well as those inherent therein. Any compounds, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A surgical cutting tool comprising:
a shank having a longitudinal axis, said shank having a perimeter surface extending around said longitudinal axis, said perimeter surface being symmetrically arranged to allow said perimeter surface to be gripped for rotation about said longitudinal axis, whereby said longitudinal axis is also a rotational axis, said shank also including a first end and a second end;
said first end of said shank including a cutter, said cutter including an outside diameter, said cutter including two or more flutes, each said flute extending parallel to said longitudinal axis and extending inward from said outside diameter, forming a recessed flute channel, each said flute channel having a pair of opposing sidewalls, each said sidewall forming a face of a cutting edge of a blade extending along the length of each said flute channel, whereby each said flute channel provides two opposing cutting edges so that said cutting tool cuts in both directions when rotationally oscillated around said rotational axis, wherein each said face includes notches for breaking said face into shorter segments.

2. The surgical cutting tool of claim 1, wherein each said blade includes a top rake, said top rake extending inwardly from said outside diameter towards said axis of rotation so that the convergence of said face and said top rake provide the outermost diameter of said cutting tool.

3. The surgical cutting tool of claim 1, wherein a top rake is formed by a radius.

4. The surgical cutting tool of claim 1 wherein said notches are offset with respect to each other from one said face to another.

5. The surgical cutting tool of claim 1, wherein a base of each said flute channel is formed as a cylindrical radius.

6. The surgical cutting tool of claim 1, wherein said cutter includes an even number of said flutes.

7. The surgical cutting tool of claim 1, wherein said cutter includes an odd number of said flutes.

8. The surgical cutting tool of claim 1, wherein said cutter is formed integral to said shank.

9. The surgical cutting tool of claim 1, wherein said cutter is cemented to said first end of said shank.

10. The surgical cutting tool of claim 1, wherein said cutter is constructed from high speed steel.

11. The surgical cutting tool of claim 1, wherein said cutter is constructed from carbide.

12. The surgical cutting tool of claim 1, wherein said cutter includes a surface coating having a higher hardness than the material constructing said cutter.

13. The surgical cutting tool of claim 12, wherein said surface coating is titanium nitride.

14. The surgical cutting tool of claim 12, wherein said surface coating is titanium carbonitride.

15. The surgical cutting tool of claim 1, wherein said shank includes a plurality of flutes to reduce the weight of said surgical cutting tool.

16. The surgical cutting tool of claim 15, wherein said shank flutes are constructed as elongated channels.

17. The surgical cutting tool of claim 16, wherein said channels include a radiused bottom surface.

* * * * *